United States Patent
Ogawa et al.

(10) Patent No.: US 7,897,645 B2
(45) Date of Patent: Mar. 1, 2011

(54) HERPESVIRUS-DERIVED THERAPEUTIC AGENT FOR PAIN

(75) Inventors: Hideoki Ogawa, Tokyo (JP); Kayako Hira, Tokyo (JP); Mamoru Kiniwa, Hanno (JP)

(73) Assignees: Taiho Pharmaceutical Co., Ltd., Tokyo (JP); Juntendo Educational Foundation, Tokyo (JP)

(*) Notice: Subject to any disclaimer, the term of this patent is extended or adjusted under 35 U.S.C. 154(b) by 509 days.

(21) Appl. No.: 11/922,593

(22) PCT Filed: Jun. 23, 2006

(86) PCT No.: PCT/JP2006/313032
§ 371 (c)(1),
(2), (4) Date: Dec. 20, 2007

(87) PCT Pub. No.: WO2007/001058
PCT Pub. Date: Jan. 4, 2007

(65) Prior Publication Data
US 2009/0149532 A1    Jun. 11, 2009

(30) Foreign Application Priority Data
Jun. 27, 2005 (JP) .............................. 2005-187185

(51) Int. Cl.
*A61K 31/16* (2006.01)
(52) U.S. Cl. .................................................. 514/629
(58) Field of Classification Search ................ 514/629
See application file for complete search history.

(56) References Cited

U.S. PATENT DOCUMENTS

| | | | |
|---|---|---|---|
| 4,556,737 A | 12/1985 | Koda et al. | ............... 564/218 |
| 6,329,428 B1 | 12/2001 | Yamauchi et al. | ........... 514/538 |
| 2003/0149105 A1* | 8/2003 | Ushio et al. | ................. 514/553 |

FOREIGN PATENT DOCUMENTS

| | | |
|---|---|---|
| JP | 11-315019 A | 11/1999 |
| JP | 2002-114672 A | 4/2002 |
| JP | 2004-292407 A | 10/2004 |
| WO | WO 0154652 A2 * | 8/2001 |

OTHER PUBLICATIONS

Tamaoki et al. "Effect of suplatast tosilat, a Th2 cytokine inhibitor, on steroid-dependent asthma: a double-blind reandomised study," The Lancet, 2000, vol. 356, pp. 273-278.*
Katakura et al. "Effect of IL-12 and soluble IL-4 receptor on the herpesvirus infection in human SCID chimeras whose Th2 cells predominate," Immunology and Cell Biology, 2004, vol. 82, pp. 421-426.*
Higa, Kazuo, et al., "Postherpetic neuralgia: diagnosis and treatment", *Pain Clinic*, vol. 25, No. 2, 2004 pp. 158-165.
Miura, Masanao, "Taijohoshintsu to Taijohoshingo Shinkeitsu" *The Journal of Therapy*, 2003, vol. 85, No. 7, pp. 2097-2104.
Yoshimura, Naoki, et al., "Targeting Afferent Hyperexcitability for Therapy of the Painful Bladder Syndrome", *Urology*, 2002, vol. 59. No. 5 Suppl., 1, pp. 61-67.
Yokota, Toshikatsu, "Mechanism of chronic pain", *Pain Clinic* vol. 22, No. 4, 2001 pp. 505-510.

* cited by examiner

Primary Examiner—Shengjun Wang
(74) Attorney, Agent, or Firm—Kubovcik & Kubovcik

(57) ABSTRACT

A therapeutic agent for treatment of herpes virus-derived pain which comprises (±)-[2-[4-(3-ethoxy-2-hydroxy-propoxy) phenylcarbamoyl]ethyl]dimethylsulfonium p-toluene-sulfonate represented by the formula (1) as an active ingredient.

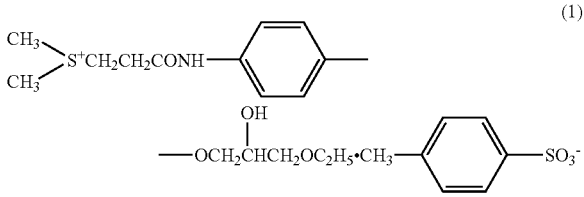

1 Claim, No Drawings

HERPESVIRUS-DERIVED THERAPEUTIC AGENT FOR PAIN

This application is a 371 of international application PCT/JP2006/313032, which claims priority based on Japanese patent application No. 2005-187185 filed Jun. 27, 2005, which is incorporated herein by reference.

TECHNICAL FIELD

The present invention relates to a therapeutic agent to treat a pain caused by a herpes virus.

BACKGROUND ART

A herpes virus is a virus that infects great majority of adults potentially and chronically, and it has a possibility of being re-activated. Typical examples of herpes virus are a simple herpes virus (herpes-simplex virus:HSV) and chicken pox-herpes zoster virus (varicella-zoster virus:VZV) both of which hide out in a sensory ganglion, an Epstein-Barr virus (EBV), a cytomegalovirus (CMV) both of which hide out in the lymphocyte in blood, etc. There are many patients who suffer from a characteristic dermatitis inflammation and pain, both of which are caused by infection and re-activation of simple herpes virus or varicella-zoster virus, and a sharp pain sometimes turns into severe sharp pain.

Among others, varicella-zoster virus causes chicken pox at first-time infection, and it hides out in a sensory ganglion, and after that it will serve as herpes zoster by re-activation. The pathology of herpes zoster is not solved completely, but if an immunity function falls by fatigue, stress, cold, pulse treatment of steroid, administration of antineoplastic drug, an operation, autoimmune disease, etc., varicella-zoster virus which was under latent infection in the sensory ganglion are re-activated. Consequently, it is thought that many adjoining nerve cells are damaged, a varicella-zoster virus is transmitted through the peripheral nerve further increasing, it infects the outer skin cell of a rule skin division, and that a characteristic dermatitis condition and sharp pain are caused. A sharp pain that appears before dermatitis is called pre-pain of "herpes zoster pain", and pain at the period of skin symptom is called "acute herpes sharp pain".

Red spots, blisters or pustules are found in the acute term and further decomposition or ulcer are presented in case of the serious illness, and skin symptom sometimes extends to the rule nerve generally. Acute herpes sharp pain is considered to be caused by the inflammation of skin, peripheral nerve, nerve solution, a ganglion or spinal rear angle, and in cases, it causes such sharp pain that patients suffer from sleep obstacle and loss of appetite.

Then, although much of acute herpes sharp pain disappears with recovery of exanthemas, at the period of six months after the symptoms of herpes appear, sharp pain remains in 10 to 15% of cases even after the recovery of exanthemas, and these cases shift to post herpetic neuralgia (abbreviated to "PHN" hereinafter). PHN is the centripetal nerve interception sharp pain of irreversible and incurable disease resulting from the nerve denaturation after inflammation, and a dangerous factor of the shift is deeply related to the condition of 50 years-old or more, prodromal pain, and further degree of seriousness of the disease, namely the degree of nerve damage (nonpatent literature 1).

A prodromal pain of herpes zoster which appears after varicella-zoster virus infection and before expression of skin symptom, a pain of the acute herpes zoster which is an inflammatory pain of acute term of herpes zoster, a post herpetic neuralgia (PHN) of nerve pain after inflammation and an after-pain of herpes zoster which appears at shifting term from a pain of the acute herpes zoster to a post herpetic neuralgia are called together "zoster-associated pain".

There are mostly burning pains, and unpleasant blunt pains like stabbing with a needle, being extracted or being bound. There are also pains close to muscular pain like stiff shoulder or lumbago, and the electrifying or torn-apart pains. With each case, the pains of these are intermingled and the character of pains also changes with progress. Cutaneous sensation of tactile sense, sense of pain and feeling of the warm and the cold decreases, and a sensitive sense called allodynia which induces sharp pain by slight touching is often caused.

PHN is said to one of the diseases with difficult medical treatment, and there is still no established cure that makes it disappear for a short period of time. Therefore, it is very important to perform a medical treatment to relief the pain during the acute term when nerve damage is reversible, and to prevent from the shift to PHN.

As a cure at the time of suffering from herpes zoster, the anti-virus treatment to varicella-zoster virus is effective first. Although mitigation of sharp pain is also expected by this medical treatment in addition to mitigation of skin condition and shortening of the disease period, the control effect of PHN shift is not proved (nonpatent literature 2). Moreover, although external application of steroid or non-steroid anti-inflammatory agent (NSAIDs) is used as relief-pain medical treatment at the acute term, the effect or preventive effect of shift to PHN is not expected. As a cure after having shifted to PHN, vitamin agents, non-narcotic analgesics, pyrine antipyretic analgesics, non-pyrine antipyretic analgesics, antidepressants, anti-spasm agents, local anesthetic agents (external application, injection), narcotic analgesics, N-methyl-D-aspartate (NMDA) receptor antagonists, capsaicin ointment, beam medical treatment, thermo-therapy, iontophoresis, nerve solution block, ultra-short waves treatment, infrared irradiation treatment and laser irradiation treatment etc. are reported. However, there is no satisfactory cure, because there are problems of side effects; the effective case are restricted; there is a problem that prognosis is not settled, etc.

An object of the present invention is to provide a medical agent which treats pain originated from herpes virus, and is excellent in the effect and little in side effect.

DISCLOSURE OF THE INVENTION

The present invention relates to the followings.

1. A therapeutic agent for treatment of herpes virus-derived pain which comprises (±)-[2-[4-(3-ethoxy-2-hydroxypropoxy) phenylcarbamoyl]ethyl]dimethylsulfonium p-toluenesulfonate represented by the formula (1) as an active ingredient.

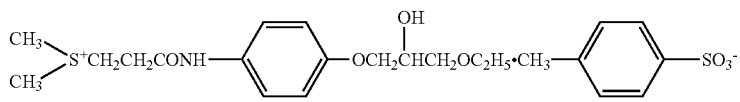

(1)

2. A therapeutic agent of the above wherein the herpes virus-derived pain is zoster-associated pain.

3. A therapeutic agent of the above wherein the zoster-associated pain is post herpetic neuralgia.

4. A therapeutic agent of the above which further contains anti-virus agent as an active ingredient.

5. A kit of compositions for treatment of herpes virus-derived pain which comprises an agent of the above containing (±)-[2-[4-(3-ethoxy-2-hydroxypropoxy)phenylcarbamoyl]ethyl]dimethylsulfonium p-toluenesulfonate of the formula (1) as an active ingredient and an agent containing an anti-virus agent as an active ingredient.

6. Use of (±)-[2-[4-(3-ethoxy-2-hydroxypropoxy)phenylcarbamoyl]ethyl]dimethylsulfonium p-toluenesulfonate of the formula (1) for producing a therapeutic agent for treatment of herpes virus-derived pain.

7. A therapeutic method of herpes virus-derived pain comprising administering to a mammal an effective amount of (±)-[2-[4-(3-ethoxy-2-hydroxypropoxy)phenylcarbamoyl]ethyl-]dimethylsulfonium p-toluenesulfonate of the formula (1).

(±)-[2-[4-(3-Ethoxy-2-hydroxypropoxy)phenylcarbamoyl]-ethyl]dimet hylsulfonium p-toluenesulfonate of the formula (1) (hereinafter abbreviated to "suplatast tosylate") has an excellent suppressant action against IgE antibody production, and is known as an agent to treat bronchial asthma, atopic dermatitis and allergic coryza (JP1991-70698B: patent literature 1). Suplatast tosylate is also known as useful for an agent to treat urination trouble (WO00/27383: patent literature 2), an itchy curative agent accompanied with kidney dialysis (JP1999-315019A: patent literature 3), an improving agent for liver function unusually caused by C type or non B non C hepatitis virus (JP2002-114672A: patent literature 4), an agent to treat chemistry substance hypersensitivity (JP2004-292407A: patent literature 5). However, it was not known at all that suplatast tosylate has an excellent effect to treat sharp pain originated from herpes virus. [Nonpatent literature 1] Pain clinic Vol. 25, No. 2, 2004, P. 158-165 [Nonpatent literature 2] Chiryo (medical treatment) Vol. 85, No. 7, 2003, P. 2097 -2104 [Patent literature 1]JP1991-70698B [Patent literature 2] WO00/27383 [Patent literature 3]JP1999-315019A [Patent literature 4] JP2002-114672A [Patent literature 5] JP2004-292407A.

Suplatast tosylate, which is the active ingredient of this invention, is a known compound, and is produced by the method described, for example, in JP1991-70689B.

The "medical treatment" as used in the present invention means the maintenance treatment for prevention and treatment of a disease as well as mitigation of condition and recurrence prevention.

The "herpes virus derived sharp pain" with effective for suplatast tosylate as used in this invention includes the sharp pain by being infected with all the viruses belonging to herpes virus family, and more concretely, sharp pain caused by infection of herpes-simplex virus and varicella-zoster virus (VZV).

In the present invention, zoster-associated pain means a prodromal pain of herpes zoster which appears after varicella-zoster virus infection and before expression of skin symptom, a pain of the acute herpes zoster which is an inflammatory pain of acute term of herpes zoster, a post herpetic neuralgia (PHN) of nerve pain of inflammation and an after pain of herpes zoster which appears at shifting term from a pain of the acute herpes zoster to a post herpetic neuralgia.

In this invention, mammal is a worm-blooded animal such as mouse, rat, rabbit, dog, cat, cow, sheep, horse, pig, monkey, human being, etc.

In this invention, anti-virus agents, vitamin agents, steroids, non-narcotic analgesics, pyrine antipyretics analgesics, non-pyrine analgesics, non-steroidal anti-inflammatory agent, anti-depressants, anti-spasm agents, narcotic analgesics, local anesthetic agents, N-methyl-D-aspartate (NMDA) receptor antagonists, capsaicin ointment, etc. are mentioned as a medicine that can be used together with suplatast tosylate. Since the medical treatment effect of a herpes virus derived sharp pain medical treatment agent not only improves further by using together or more with these agents, but the amount of medication can be reduced compared with the case where it is used by the medicine independent which can be used together, it is suitable also from the view point of mitigation of side effects. Moreover, nerve block, beam medical treatment, thermo-therapy, iontophoresis, nerve solution block, ultra short-waves treatment, infrared irradiation treatment and laser irradiation treatment etc. may be used together with.

Examples of anti-virus agents are acyclovir, azidouridine, ansamycin, amantadine, bromovinyldeoxyuridine, chlorovinyldeoxyuridine, cytarabine, didanosine, deoxynojirimycin, dideoxycytidine, dideoxyinosine, dideoxynucleoside, desciclovir, deoxyacyclovir, edoxudine, enviroxime, valaciclovir, fiacitabine, foscarnet, fialuridine, fluorothymidine, floxuridine, ganciclovir, hypericin, interferon, interleukin, isethionate, idoxuridine, nevirapine, pentamidine, ribavirin, rimantadine, stavirdine, sargramostim, suramin, tricosanthin, trifluorothymidine, tribromothymidine, trichlorothymidine, vidarabine, zidoviridine, zalcitabine, 3-azido-3-deoxythymidine and a pharmaceutically acceptable salt thereof.

Examples of especially preferable anti-virus agents are acyclovir, ganciclovir, valaciclovir, vidarabine and a pharmaceutically salt thereof.

Examples of vitamins are vitamin A, vitamin D, vitamin B analogs, (B1, B2, B6, B12), Niacin, folic acid, pantothenic acid, vitamin C, vitamin E, biotin and vitamin K, and more specifically preferable examples are retinol, a carcidole, carcitriol, tacarcitriol, carcipotriol, maxacarcitol, falecarcitol, thiamine, cocarboxylase, fursultiamine, prosultiamine, octotiamine, thiaminedisulfide, bisbentiamine, bisibutiamine, benfotiamine, cetitiamine, riboflavin, flavine adenine dinucleotide, pyridoxine, pyridoxal, nicotinic acid, nicotinamide, cyanocobalamin, cobamamide, mecobalamin, folic acid, calcium pantothenate, panthenol, panthetin, ascorbic acid, tocophenol, biotin, phytonadione, menatetrenone or a pharmaceutically acceptable salt thereof.

Examples of steroids are prednisolone, methylprednisolone, hydrocortisone, flumetasone, triamcinolone, triamcinolone acetonide, dexamethasone, fluocinolone, fluocinolone acetonide, betamethasone, beclometasone, clobetasone, fludroxycortide, fluocinonide, halcinonide, amcinonide, difluprednate, diflucortolone, diflorasone, clobetasol, cortisone, hydrocortisone sodium, fludrocortisone, prednisolone sodium, halopredone, methylprednisolone sodium, dexamethasone sorium, paramethasone, mometasone, deprodone, alclometasone and a pharmaceutically acceptable salt thereof.

Examples of non-narcotic analgesics are pentazocine, tramadol, butorphanol, buprenorphine, eptazocine and a pharmaceutically acceptable salt thereof.

Examples of pyrine antipyretic analgesics are sulpyrine and a pharmaceutically acceptable salt thereof.

Examples of non-pyrine antipyretic analgesics are acetaminophen, dimetotiazine and a pharmaceutically acceptable salt thereof.

Examples of non-steroidal anti-inflammatory agents are sodium salicylate, acetylsalicylic acid, salicylamide, flufenamic acid, mefenamic acid, tolfenamic acid, diclofenac, sulindac, fenbufen, amfenac, indometacine, proglumetacin, acemetacin, nabumetone, etodolac, mofezolac, ibuprofen, ketoprofen, flurbiprofen, oxaprozin, fenobufen, tiaprofenic acid, naproxen, pranoprofen, loxoprofen, alminoprofen, zaltoprofen, bucolome, piroxicam, ampiroxicam, tenoxicam, lornoxicam, epirizole, tiaramide, emorphan and a pharmaceutically acceptable salt thereof.

Examples of anti-depressants are nortriptyline, amoxapine, maprotiline, imipramine, amitriptyline, trimipramin, clomipramine, lofepramin, dosulepin, trazodon, fluvoxamine, paroxetine, milnacipran, mianserin, setiptiline, sulpiride and a pharmaceutically acceptable salt thereof.

Examples of anti-spasm agents are phenytoin, ethotoin, phenobarbital, primidone, valproic acid, carbamazepin, trimethadione, ethosuximide, acetylpheneturide, sultiame, diazepam, clonazepam, clobazam, zonisamide, acetazolamide and a pharmaceutically acceptable salt thereof.

Examples of narcotic analgesics are opium, opium-ipecac acid, opium alkaloid, opium alkaloid-atropine, opium alkaloid-scopolamine, morphine, morphine-atropine, ethyl morphine, oxycodone, oxycodone-atropine, codeine, dihydrocodeine, oxymetebanol, cocaine, pethidine, fentanyl, methamphetamine and a pharmaceutically acceptable salt thereof.

Examples of local anesthetics are ropivacaine, lidocaine, procaine, propitocaine, bupivacaine, mepivacaine, dibucaine, dibucaine-diethylaminoethyl p-butylaminobenzoate, tetracaine, oxybuprocaine and a pharmaceutically acceptable salt thereof.

Examples of NMDA receptor antagonists are ketamine, amantadine, dextromethorphan, ifenprodil, memantine and a pharmaceutically acceptable salt thereof.

Examples of pharmaceutically acceptable salts in this invention are inorganic acid salt such as hydrochloride, sulfate, tartarate, hydrobromide, nitrate or phosphate; organic acid salt such as propionate, dipropionate, valerianate, butyrate, pivalate, acetate, benzoate, mesylate, trifluoroacetate, tartarate, succinate, parmitate, citrate, malate, maleate, fumalate, methanesulfonate, benzenesulfonate, toluenesulfonate or nicotinate; and inorganic salt such as potassium salt, sodium salt, calcium salt or aluminum salt. When hydrates may be formed depending on the nature of compound, they are also within the scope of this invention.

The therapeutic agent for treatment of herpes virus-derived pain of the present invention can be administered to a mammal in a variety of administration forms. These include, for example, oral preparations, injections, suppositories per rectum, and external preparations (such as ointments, plasters, eye drops, etc.). These preparations may be prepared by customary methods per se known by persons skilled in the art. Among oral preparations, solid preparations are prepared, suplatast tosylate is mixed with a vehicle, and optionally, a binder, a disintegrant, a lubricant, a colorant, a sweetener, a flavoring agent, or similar agents, and the resultant mixture is processed into tablets, coated tablets, granules, powders, capsules, dry syrups, etc. by customary methods. When oral liquid preparations are manufactured, suplatast tosylate is mixed with a sweetener, a buffer, a stabilizer, a flavoring agent, or similar agents, and the resultant mixture is processed into, by customary methods, liquid medicines, syrups, etc.

When injections are manufactured, suplatast tosylate is mixed with a pH regulator, a buffer, a stabilizer, an isotonic agent, a local anesthetic drug, or similar agents, and the resultant mixture is processed into injection products for subcutaneous injection, intramuscular injection, or intravenous injection.

Suppositories per rectum are prepared by mixing suplatast tosylate with an excipient, optionally with a surfactant, etc., followed by a routine process for manufacturing suppositories.

Among external preparations, ointments, such as in the form of paste, cream, or gel, are prepared, by mixing a base containing suplatast tosylate with, as required, a stabilizer, a humectant, a preservative, etc., by customary methods. Examples of bases include white Vaseline, paraffin, glycerin, cellulose derivatives, polyethylene glycol, silicone, and bentonite. Examples of preservatives include methyl paraoxybenzoate, ethyl paraoxybenzoate, and propyl paraoxybenzoate.

When plasters are produced, the above-mentioned ointment, cream, gel, paste, etc. are applied onto a customary support by a known method. Supports are preferably woven or nonwoven fabrics made of cotton, staple fiber, or chemically synthetic fiber, and films and foamed sheets prepared from soft vinyl chloride, polyethylene, or polyurethane.

The medicine which can be used together can also be made into the same application form as suplatast tosylate mentioned above.

Therefore, when using two or more ingredients with the medicine that can be used together with suplatast tosylate, it can be administered in a single application form containing these ingredients, and can also be administered in two or more administration forms containing the respective ingredients. In cases two or more administration forms, they may be as a kind of forms of the same administration route (for example, both oral dosage forms) which may further form a kit, or may be different kinds of forms (for example, one is oral dosage form and the another is injection form) which may further form a kit. Moreover, as long as the purpose of this invention is reached, the present tablets prepared separately may be administered simultaneously or differently according to time lags to the patient, and a number of times of administration per day of each dosage form may be different.

The amount of suplatast tosylate to be incorporated into the above-mentioned dosage forms varies with the patient's symptoms, dosage form etc. It is generally preferred that suplatast tosylate be incorporated into a unit dosage in an amount of about 5 to 1,000 mg for oral agents, about 0.1 to 500 mg for injections, and about 5 to 1,000 mg for suppositories and external agents.

Although the daily dose of suplatast tosylate may also differ depending on the symptoms weight, age, sex or other conditions of a patient, it is preferably about 5 to 1000 mg.

Moreover, although the amount of anti-virus agent is suitably determined by the kind of the agent when an anti-virus agent is used together, it is usually about 0.1 to 10000 mg per day, and it may be reduced gradually.

BEST MODE OF CARRYING OUT THE INVENTION

The present invention will be described below in more detail with reference to examples and test examples. However, the invention is not limited by these examples. The sharp pain in examples was evaluated by the Visual Analogue Scale evaluation (hereinafter abbreviated to "VAS evaluation"), in which the grade of pain of each patient is expressed by himself or herself on a 100 mm straight line. In VAS evaluation, the highest score is 10 points (100 mm), and the point becomes smaller according to the decrease of the pain. (refer to Anesth Analog 1993, 77, 1041-1047 etc.)

PREPARATION EXAMPLE 1 (TABLET)

suplatast tosylate 50 mg
corn starch 50 mg
microcrystalline cellulose 50 mg
hydroxypropyl cellulose 15 mg
lactose 47 mg
talc 2 mg
magnesium stearate 2 mg
ethyl cellulose 30 mg
unsaturated glyceride 2 mg
titanium dioxide 2 mg Tablets (50 mg of suplatast tosylate/tablet) of the above-described composition were prepared by employing a conventional method.

PREPARATION EXAMPLE 2 (GRANULE)

suplatast tosylate 300 mg
lactose 540 mg
corn starch 100 mg
hydroxypropyl cellulose 50 mg
talc 10 mg Granules (300 mg of suplatast tosylate/package) of the above-described composition were prepared by employing a conventional method.

PREPARATION EXAMPLE 3 (CAPSULE)

suplatast tosylate 100 mg
lactose 30 mg
corn starch 50 mg
microcrystalline cellulose 10 mg
magnesium stearate 3 mg Capsules (100 mg of suplatast tosylate/capsule) of the above-described composition were prepared by employing a conventional method.

PREPARATION EXAMPLE 4 (INJECTION)

suplatast tosylate 100 mg
sodium chloride 3.5 mg
distilled water suitable amount Injections (100 mg of suplatast tosylate/2 ml ampule) of the above-described composition were prepared by employing a conventional method.

PREPARATION EXAMPLE 5 (DRY SYRUP)

suplatast tosylate 50 mg
purified sucrose 949 mg
fragrance suitable amount

A dry syrup (50 mg of suplatast tosylate/package) of the above-described composition was prepared by employing a conventional method.

PREPARATION EXAMPLE 6 (SYRUP)

suplatast tosylate 50 mg
purified sucrose 1000 mg
ethyl para-hydroxybenzoate 1 mg
purified water suitable amount
fragrance suitable amount
colorant suitable amount A syrup (50 mg of suplatast tosylate/2 ml) of the above-described composition was prepared by employing a conventional method.

PREPARATION EXAMPLE 7 (SUPPOSITORY)

suplatast tosylate 300 mg
Witepsol W-35 1400 mg
(Witepsol: registered trademark, product of Dynamite Nobel AG: a mixture of mono-, di-, and tri-glycerides of saturated fatty acids which encompass those acids from lauric acid to stearic acid)

Suppositories (300 mg of suplatast tosylate tosylate/piece) of the above-described composition were prepared by employing a conventional method.

PREPARATION EXAMPLE 8 (TABLET)

suplatast tosylate 100 mg
acyclovir 200 mg
corn starch 45 mg
microcrystalline cellulose 50 mg
hydroxypropyl cellulose 15 mg
lactose 47 mg
talc 2 mg
magnesium stearate 2 mg
ethyl cellulose 30 mg
unsaturated glyceride 2 mg
titanium dioxide 2 mg Tablets (50 mg of suplatast tosylate and 200 mg of acyclovir/tablet) of the above-described composition were prepared by employing a conventional method.

PREPARATION EXAMPLE 9 (KIT)

<Hard Capsule Containing Suplatast Tosylate>
suplatast tosylate 100 mg
lactose 50 mg
corn starch 47 mg
crystalline cellulose 50 mg
talc 2 mg
magnesium stearate 1 mg Hard capsules (100 mg of suplatast tosylate/capsule) of the above-described composition were prepared by employing a conventional method.

<Tablet Containing Valaciclovir Hydrochloride>
Valaciclovir hydrochloride 556 mg
crystalline cellulose 100 mg
hydroxypropyl cellulose 30 mg
magnesium stearate 5 mg
macrogol 5 mg
titanium dioxide 4 mg Tablets (556 mg of Valaciclovir hydrochloride/tablet) of the above-described composition were prepared by employing a conventional method.

The above hard capsule containing suplatast tosylate and the tablet containing Valaciclovir hydrochloride were made into a single package.

EXAMPLE 1

A female of 63 years old. The painful rashes were found at lower left abdomen, buttock and the thigh, and she was diagnosed as herpes zoster. Then, although skin rash was recovered and the strong pain was mitigated with time, the dull pain continued, and therefore oral administration of mecobalamin of 1500 μg/day was continued. The progress of neuralgia after herpes zoster had not changed for 3 years after the consultation (5 points at VAS evaluation), oral administration of a 100 mg capsule of IPD (brand name) (generic name: suplatast tosilate) [Taiho Pharmaceutical Co. Ltd.] 3 times per day was started. After 3 days of the administration of suplatast tosylate, post herpetic neuralgia disappeared, and VAS evaluation became 0 point.

EXAMPLE 2

A female of 70 years old. The patient complained sense of incongruity from the right chest to the abdomen, and 5 days thereafter the painful rashes were observed at the same region. Then she was diagnosed as herpes zoster. The skin rashes got better by dropping of anti-virus agent and was finally recovered, but dull pain and sense of incongruity remained, and therefore internal administration of mecobalamin of 1500 μg/day was continued. The progress of post herpetic neuralgia did not change for 8 months after the consultation (7 points at VAS evaluation), oral administration of a 100 mg capsule of IPD 3 times per day was started in the same manner as in Example 1. After 1.5 months of the administration of suplatast tosylate, the post herpetic neuralgia decreased, and VAS evaluation became 2 points.

EXAMPLE 3

A female of 26 years old. She was diagnosed as right face herpes zoster. Anti-virus agent was administered by drops for 5 days. Since dull pain remained at the same region thereafter, oral administration of mecobalamin of 1500 μg/day and sodium loxoprofen of 180 mg/day was started after the consultation. After administration for 2 weeks, VAS evaluation of pain dropped to 1 point, and the administration of sodium loxoprofen stopped with administration of mecobalamin maintained. Mecobalamin was further administered, and although VAS evaluations were 1 to 3 points for about 3 months, sense of incongruity and spasmodic sharp pain of neuralgia after herpes zoster continued, and therefore oral administration of a 100 mg capsule of IPD 3 times per day was started in the same manner as in Example 1 with administration of mecobalamin maintained. After 1 week of the administration of suplatast tosylate, the post herpetic neuralgia disappeared, and VAS evaluation became 0 point. Oral administration of suplatast tosylate and mecobalamin was continued for further about 1 month, and no symptom was observed. Then administration was stopped.

EXAMPLE 4

A female of 76 years old. Sharp pain appeared from left axilla to the left back, and then, 5 days after that small blister with red ring appeared. She was diagnosed as herpes zoster by consultation and was administered anti-virus agent for 1 week. However, pain continued (5 points at VAS evaluation), and administration of mecobalamin of 1500 μg/day was started after 2 weeks of the consultation. After administration of mecobalamin for 1.5 months, oral administration of sodium flaviadeninedinucleotide and pyridoxal phosphate, and ultra short-waves treatment were added because post herpetic neuralgia still remained in spite of the estimation of 0.5 to 1 point at VAS evaluation. But, neuralgia did not disappear completely after the treatments for 3 months. Then oral administration of a 100 mg capsule of IPD 3 times per day was started in the same manner as in Example 1, and after the administration for 1 month, the post herpetic neuralgia decreased. VAS evaluation became 0.1 to 0.2 point.

EXAMPLE 5

A female of 67 years old. She was diagnosed as herpes zoster of left upper limb and left shoulder to the back, and anti-virus agent was administered orally for 1 week, but post herpetic neuralgia remained (5 points at VAS evaluation) for about 1.5 months. Then oral administration of a 100 mg capsule of IPD 3 times per day was started in the same manner as in Example 1, the post herpetic neuralgia decreased to 1 point at VAS evaluation, and further decreased to 0.7 point at VAS evaluation by continuation of the administration.

EXAMPLE 6

A male of 68 years old. Painful rashes appeared from right chest to the back, and he was diagnosed as herpes zoster. Anti-virus agent was administered by dropping for 1 week, but the pain continued. Diclofenac sodium suppository was used by 1 to 2 times per day in addition to administration of morphine hydrochloride 30 mg/day, but both of them were no effect, and further nerve block treatment was also no effect. After 6 months of the consultation (7 points at VAS evaluation), oral administration of a 100 mg capsule of IPD 3 times per day was started in the same manner as in Example 1, the post herpetic neuralgia decreased to 5 points at VAS evaluation by the treatment for 3 weeks, although the administration of morphine was invalid.

INDUSTRIAL APPLICABILITY

The therapeutic agent of the present invention shows an excellent effect in treatment of herpes virus-derived pain and little side effect, and is extremely useful.

The invention claimed is:

1. A therapeutic method of post herpetic neuralgia comprising administering to a mammal an effective amount of (±)-[2-[4-(3-ethoxy-2-hydroxypropoxy) phenylcarbamoyl] ethyl]-dimethylsulfonium p-toluenesulfonate of the formula (1)

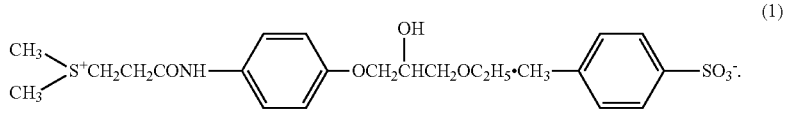

* * * * *